US00PP12010P2

(12) United States Plant Patent
Magee

(10) Patent No.: US PP12,010 P2
(45) Date of Patent: Jul. 24, 2001

(54) ILEX HYBRID PLANT NAMED 'CONOT'

(75) Inventor: Jack Mitchell Magee, Poplarville, MS (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 09/440,256

(22) Filed: Nov. 15, 1999

(51) Int. Cl.[7] ..... A01H 5/00
(52) U.S. Cl. ..... Plt./247
(58) Field of Search ..... Plt./247

*Primary Examiner*—Bruce R. Campell
*Assistant Examiner*—A Para

(57) ABSTRACT

A new and distinct variety of Ilex plant found as an openly pollinated seedling of Ilex Hybrid 'Mary Nell'. The new variety possesses a dense, upright, pyramidal growth habit, an abundance of attractive orange-red fruit, glossy dark green foliage, and distinctly arranged leaf serrations.

1 Drawing Sheet

BACKGROUND OF THE INVENTION

This new variety was found as an openly pollinated seedling of Ilex Hybrid 'Mary Nell', an unpatented variety, maintained in the Evergreen Nursery at Poplarville, Miss. The seedling was found in May, 1989. The new and distinct Ilex Hybrid plant of this invention comprises a novel and valuable holly plant with an upright, pyramidal shape, an abundance of attractive orange-red fruit, and unusual leaf serrations. As with the parent plant, the plant of this invention may be advantageously employed as a specimen appointment, in either formal or informal groupings, and is very attractive in mass plantings. The plant serves well in foundation plantings and is adapted for culture as a potted plant. This plant is responsive to pruning and training and may be used in forming attractive hedges and maintained without an excessive amount of care.

Asexual propagation of the new plant by cuttings has been under Mr. Jack Mitchell Magee's direction at the same location. Several generations of the new plant have been evaluated and the distinctive characteristics of the plant have remained stable. The plant cannot be reproduced true from seed.

SUMMARY OF THE INVENTION

The following are the most outstanding and distinguishing characteristics of this new cultivar when grown under normal horticultural practices in Poplarville, Miss.

1. Dense, upright, and pyramidal in nature.
2. Hardy to Zone 7.
3. Heat and drought tolerant.
4. Fast growth rate under normal fertilization and moisture conditions.
5. Tolerates most soils from moist to dry and from sand to clay.
6. Relatively pest resistant.
7. Very desirable in planters.
8. Makes a good hedge or screen.
9. Easy to root from cuttings collected any time of year.
10. Produces an abundant amount of attractive orange-red fruit in the fall which persist into the winter and which may result in bird visitations.

11. Has the ability to be sheared and trimmed to be kept within prescribed limits.
12. Mature leaves are a glossy rich green color with attractive spines.
13. Easily trained into a small tree.

DESCRIPTION OF THE DRAWINGS

This new Ilex Hybrid variety is illustrated by the accompanying photographic prints in which.

1.

2.

Figure 1:
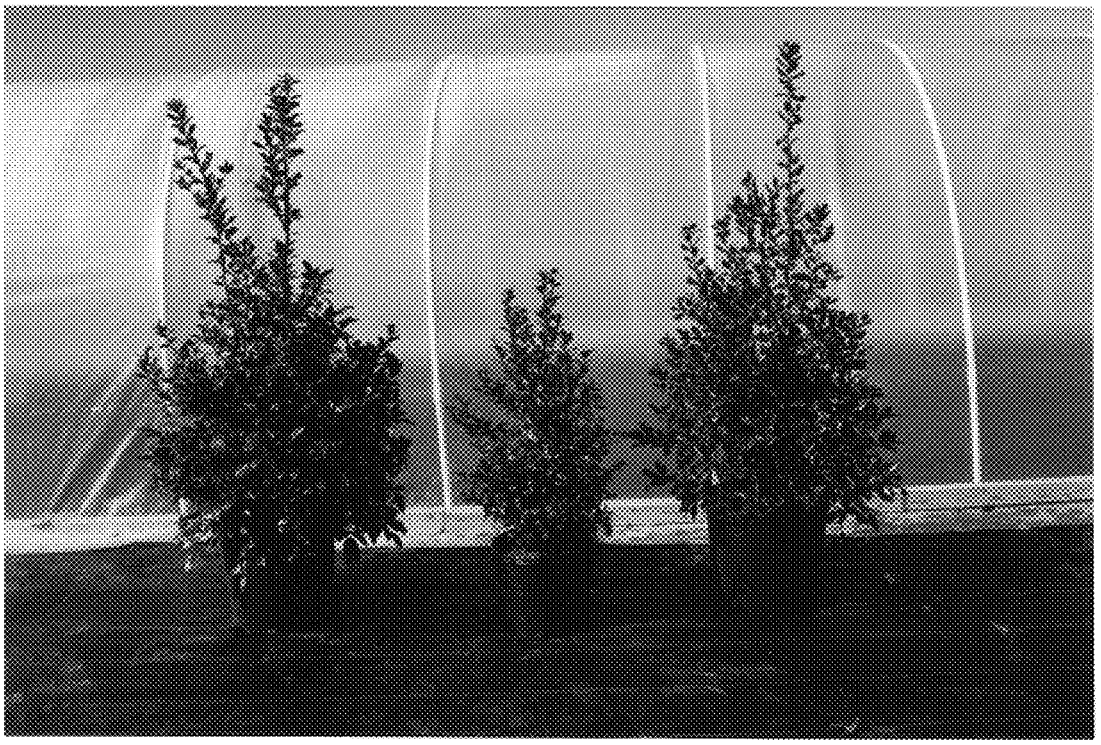
FIG. 1 is a side-by-side photograph of (from left to right) the parent plant Ilex Hybrid 'Mary Nell', the new variety, and Ilex hybrid 'Nellie R. Stevens'. The mid-winter photograph shows the new variety's dense, upright, pyramidal shape.
Figure 2:
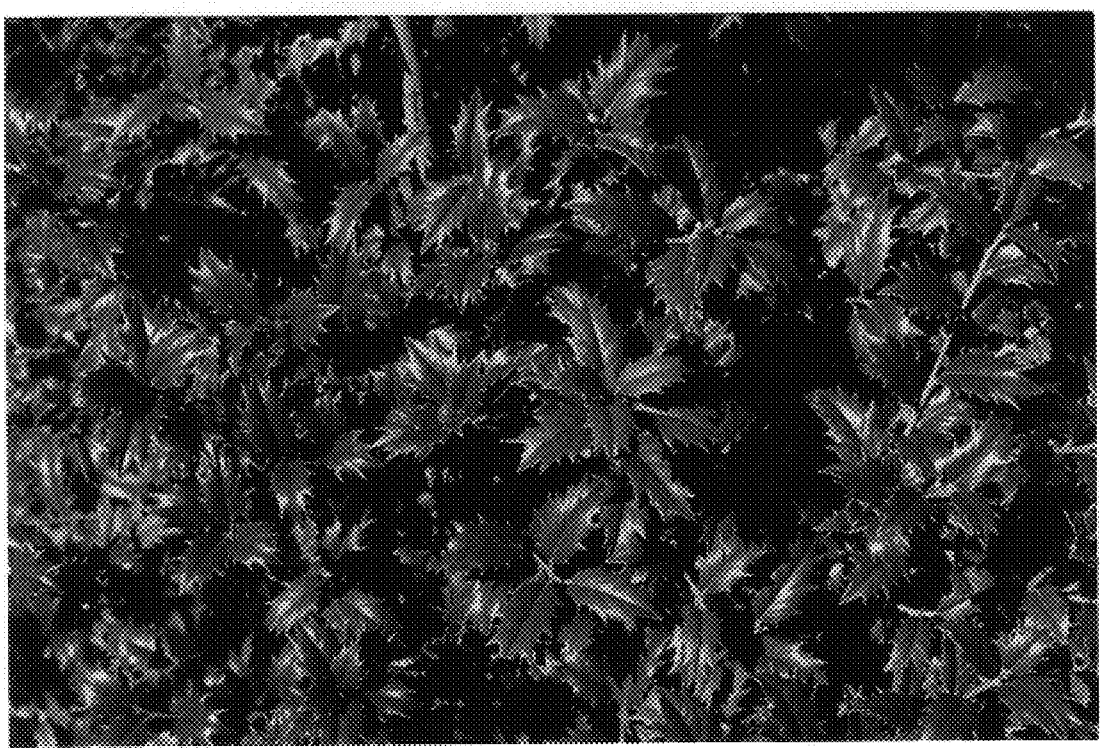
FIG. 2 shows a close-up view of the attractive orange-red fruit and mature foliage of the new variety.

The colors shown are as true as is reasonably possible to obtain by conventional photographic procedures. The colors of the various plant parts are defined with reference to The Royal Horticultural Society Colour Chart. Descriptions of colors in ordinary terms are presented where appropriate for clarity in meaning.

BOTANICAL DESCRIPTION OF THE PLANT

The following is a detailed description of the new variety of Ilex based on my observations made of plants grown in commercial production practices, in greenhouses, and in established landscape plantings in Poplarville, Miss.

Distinctive Characteristics:

| Characteristic | 'Conot' | 'Mary Nell' | 'Nellie R. Stevens' |
|---|---|---|---|
| Height (Mature) | 12–15' | 15–20' | 15–25' |
| Width (Mature) | 8–10' | 12–15' | 12–15' |
| Leaf Length | 1½–2¼" | 2⅝–3½" | 2¼–3" |
| Leaf Width | ⅞–1⅜" | 1⅛–1¾" | 1–1½" |
| Leaf Glossiness (Mature) | Glossy | Very Glossy | Glossy |
| Leaf Shape | Elliptic to elliptic lanceolate | Ovate to broadly lanceolate | Ovate |

-continued

| Distinctive Characteristics: | | | |
|---|---|---|---|
| Characteristic | 'Conot' | 'Mary Nell' | 'Nellie R. Stevens' |
| Leaf Spines (Pairs) | 6–9 | 9–11 | 2–3 |
| Leaf Base | Acute | Obtuse | Obtuse |
| Fruit Color | Orange-Red G. 33A | Red G. 40A | Orange-Red G. 33A |
| Fruit Size | ¼–⅜" | ⅜–7/16" | ⅜–½" |
| Mature Shape | Dense, upright pyramidal | Upright, pyramidal | Upright, pyramidal, rounded with age |
| Hardiness | Zone 7 | Zone 7 | Zone 6 |

The parent plant of the new variety 'Conot' is Ilex Hybrid 'Mary Nell' (unpatented) which originated from a controlled cross made in 1962 by Joe McDaniel in Semmes, Ala. The female parent was *Ilex cornuta*×*Ilex pernyi* 'Red Delight' (unpatented), a selection of Henry Hohman, Kingsville, Md. The male parent was *Ilex latifolia*. Ilex 'Mary Nell' was named in 1981 by Thomas H. Dodd, Jr. after Joe McDaniel'wife.

*Ilex aquifolium*×*Ilex cornuta* 'Nellie R. Stevens' is very popular in the industry. It was released by G. A. Van-Lennep, Jr., St. Michael, Md. in 1954. It is named for the owner, Nellie R. Stevens, Oxford, Md. This non-patented plant is comparable to the new plant; however, there are many differences, the most obvious being the foliage shape and number of spines.

It is from the openly pollinated seedlings of the Ilex 'Mary Nell' plant that I found the new plant. This new variety will be sold under the Trademark name Patriot. It will be listed as Ilex Hybrid Patriot TM 'Conot'.

Classification:

*Botanical.*—(*Ilex cornuta*×*Ilex pernyi*)×*Ilex latifolia*, 'Conot'.

*Form.*—Dense,upright, and pyramidal.

*Height.*—12–15'.

*Width.*—8–10'.

*Growth habit.*—Shrub or small tree. Fast growth rate under normal fertilization and moisture conditions.

*Foliage.*—Alternate, simple, evergreen, elliptic to elliptic lanceolate, and varying in size from 1½" to 2¼" long and ⅞" to 1⅜" wide. The margins are slightly convex and serrate with 6 to 9 pairs of prominent spines.

The spines vary in length and width from 1/16 to ⅜". The apex is acute and triangular with 3 prominent spines. The terminal spine is slightly larger than the next pair and points downward at an angle to the main leaf blade. Spines alternate between long and short after this first pair. The base of the leaf is obtuse. The petiole is 3/16 to ¼" long. Mid-veins and laterals are impressed on the upper leaf surface and the mid-veins are prominent on the underside. Immature mid and lateral veins are Yellow-Green Group 144B top and bottom and mature to Yellow-Green Group 146D. The upper surface of the immature leaf is glossy, glabrous, and is Yellow-Green Group 144A. The lower surface of the immature leaf is Yellow-Green Group 144A and matte. As the leaves mature the upper surface becomes Green Group 139A and the lower leaf surface becomes Yellow-Green Group 146C. This mature leaf color persists throughout the winter. The degree of glossiness of the mature leaf is slightly less than that of the parent plant.

In 1994, the date of initial spring growth was March 14, in Poplarville, Miss. After the spring flush, there was almost continuous growth until fall, ending October 28, also in Poplarville, Miss. This growth pattern was identical to the parent plant. When grown in full sun, the internode length of this plant is ½" to ¾" compared to ⅝ to 1¼" for the parent plant. When grown in light shade, the internode length is ¾" to 1". As would be expected, either plant grown in the shade results in a taller, less dense plant with larger leaves.

The average length of terminal growth of the initial spring flush is about 10" for a plant in full sun and about 12" when grown in shade. After this initial flush we normally trim the plant lightly and the plant then continues to grown about 6" until we trim it a second time in the early fall. The fall growth of about 8" then hides the cut limbs. We finish in the fall with a three gallon plant about 28" tall and 24" wide. I have not noticed a difference in vigor between this plant and the parent. In the landscape, little or no pruning is necessary to produce a dense and pyramidal shrub in full sun. In shade, however, some trimming may be needed to produce the same effect. The lower limbs can be removed to produce a small tree with attractive gray-brown bark.

Stems: The young shoots and petioles are Yellow-Green Group 144A, glabrous, and matte. After one or more years the stems are generally Grey-Brown Group 199C, glabrous and rugose. The pith is solid and uniform.

Flowers: Small, creamy yellow, inconspicuous, slightly fragrant, borne on previous season's growth from March to May. Flower structure of this plant is identical to that of the parent plant. Buds are globular, 1/16 to ⅛" diameter, Yellow-Green Group 144A, and without foliaceous appendages. Flowers are clustered in the leaf axils and are 4-merous. Unbranched pedicels are about ¼" long and Yellow-Green Group 144A. The four ovate petals are 1/16" to ⅛" wide, ⅛ to 3/16 long, Yellow Group 2D, arranged regularly, united at the base, and imbricate in bud. The ovary protrudes from the receptacle and is Green Group 143A. There are four ⅛" long stamens with underdeveloped anthers which are White Group 155D. No pollen is produced. Blooms are small to medium in size, Yellow Group 2D, ⅜" in diameter, and last on the plant in the garden two to four days.

Fruit: Drupaceous, globose, ¼ to ⅜" diameter, borne fasciculate with two to five fruits on short unbranched pedicels ¼" long. Each fruit contains four pyrenes. Matures to Orange-Red Group 33A in mid-November in Poplarville, Miss. and persists into the winter. Normally, fruit set is heavy.

Culture: Grows well in a wide range of conditions and tolerates sun to part shade. Grows in nearly any soil type, from moist to very dry and sand to clay. Responds well to mulching and medium applications of fertilizer; prefers PH 5 to 6.5. Little pruning is needed. Can be sheared. Disease and pest resistance are comparable to Ilex 'Mary Nell'. Propagated with semi-hardwood cuttings any time of year. Cuttings taken in late spring initiate roots in 6 to 8 weeks and are well rooted in 4 to 5 months. The root system is fibrous and rapidly established.

I claim:

1. A new and unique variety of Ilex plant named 'Conot', as illustrated and described.

* * * * *